US00PP27119P2

(12) United States Plant Patent
Dofferhoff

(10) Patent No.: US PP27,119 P2
(45) Date of Patent: Aug. 30, 2016

(54) ***HELLEBORUS* PLANT NAMED 'AMOR'**

(50) Latin Name: *Helleborus hybridus*
Varietal Denomination: Amor

(71) Applicant: Hans Dofferhoff, Reeuwijk (NL)

(72) Inventor: Hans Dofferhoff, Reeuwijk (NL)

(73) Assignee: KWEKERIJ DE BOEZEM B.V., Reeuwijk (NL)

( * ) Notice: Subject to any disclaimer, the term of this patent is extended or adjusted under 35 U.S.C. 154(b) by 0 days.

(21) Appl. No.: 14/544,596

(22) Filed: Jan. 26, 2015

(51) Int. Cl.
*A01H 5/02* (2006.01)

(52) U.S. Cl.
USPC ..... Plt./439

(58) Field of Classification Search
USPC ..... Plt./263.1, 439
See application file for complete search history.

(56) References Cited

PUBLICATIONS

PLUTO: Plant Variety Database, Feb. 9, 2016, citation for 'Amor'. 1 page.*

New plants and flowers website (http://www.newplantsandflowers.com/earliest-red-hellebore/). Feb. 9, 2016. 1 page.*

* cited by examiner

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Helleborus*, 'Amor', that is characterized by its early flowering habit; blooming for 8 weeks beginning in late fall in The Netherlands, its large flowers up to 6 cm in diameter that are reddish purple in color and yellow-green at the base, and its large and durable leaves.

2 Drawing Sheets

Botanical classification: *Helleborus hybridus*.
Cultivar designation: 'Amor'.

BACKGROUND OF THE INVENTION

The present invention relates to a new and distinct cultivar of *Helleborus* plant, botanically known as *Helleborus hybridus* 'Amor' and will be referred to hereafter by its cultivar name, 'Amor'. The new cultivar represents a new herbaceous perennial grown for landscape use.

The new invention arose as part of an ongoing breeding project by the Inventor in Reeuwijk, The Netherlands. The objectives of the breeding include obtaining new cultivars of *Helleborus* that exhibit early flowering habits.

The new cultivar of *Helleborus*, 'Amor', arose from a cross made in December of 2000. An unnamed and unpatented proprietary seedling from the Inventor's breeding program was pollinated with a mixture of pollen from unnamed and unpatented proprietary plants from the Inventor's breeding program. The exact male parentage is therefore unknown. 'Amor' was selected as a single unique plant in November of 2007.

Asexual propagation of the new cultivar was first accomplished by the Inventor by division in Reeuwijk, The Netherlands in January of 2009. Asexual propagation by division and tissue culture has been determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Amor' as a unique cultivar of *Helleborus*.

1. 'Amor' exhibits an early flowering habit; blooming for 8 weeks beginning in late fall in The Netherlands.
2. 'Amor' exhibits large flowers up to 6 cm in diameter that are reddish purple in color with yellow-green at the base.
3. 'Amor' exhibits large and durable leaves.

The female parent of 'Amor' differs from 'Amor' in having leaves that are smaller in size and in having flowers that are smaller in size. The new cultivar can be most closely compared to the *Helleborus* hybrid cultivars 'COSEH 950' (U.S. Plant Pat. No. 24,289) and 'COSEH 970' (U.S. Plant Pat. No. 24,310). 'COSEH 950' differs from 'Amor' in having a shorter plant height and in having sepals that are brown-green in color at the base. 'COSEH 970' differs from 'Amor' in having a shorter plant height and in having sepals that are grayed red and tinged with yellow-green in color.

BRIEF DESCRIPTION OF THE DRAWINGS

The accompanying colored photographs illustrate the overall appearance and distinct characteristics of the new *Helleborus*. The photographs were taken of a two year-old plant of the new cultivar as field grown in Reeuwijk, The Netherlands and placed in a container for the photographs.

The photograph in FIG. 1 provides a side view of 'Amor' in bloom.

Figure 1:
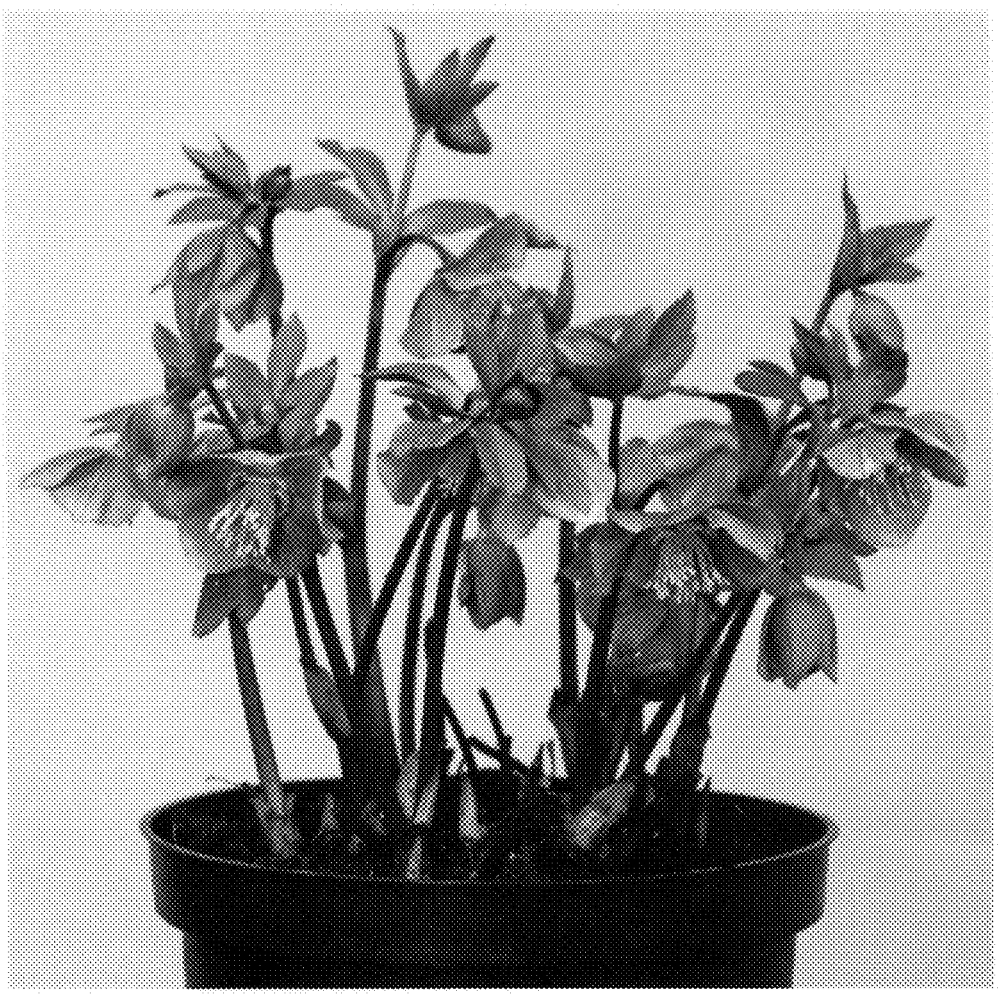
Figure 2:
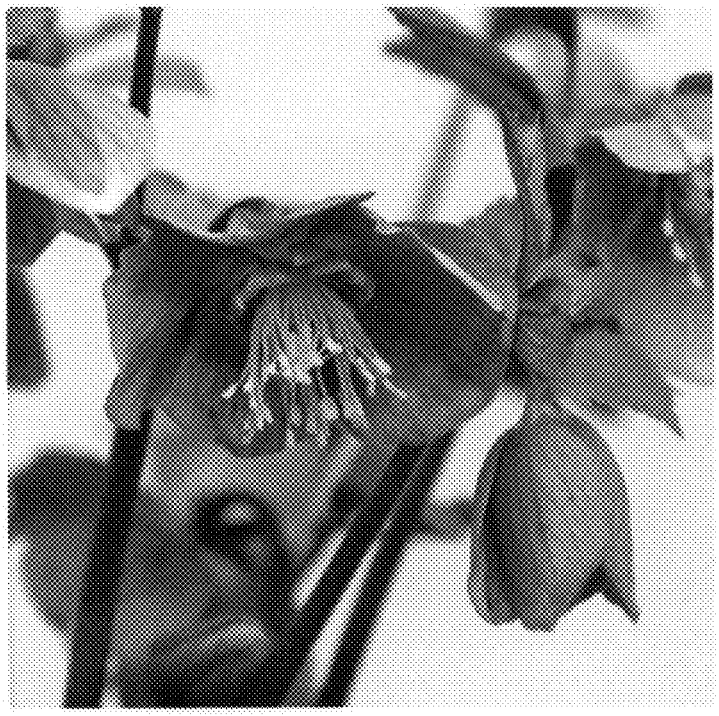

The photograph in FIG. 2 provides a close-up view of a flower of 'Amor'.

Figure 3:
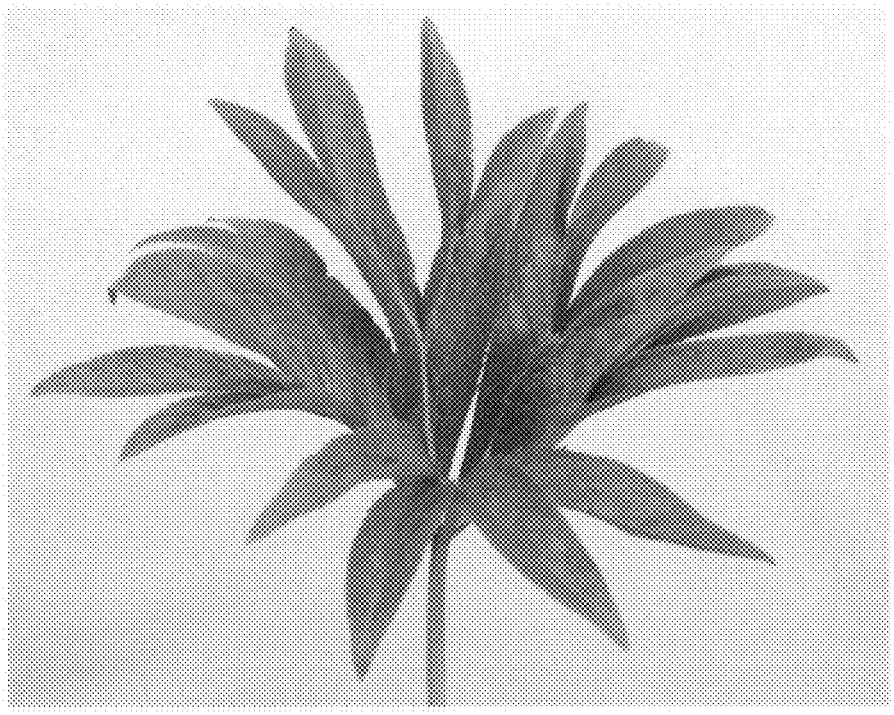

The photograph in FIG. 3 provides a close-up view of the foliage of 'Amor'.

The colors in the photographs are as close as possible with the digital photography and printing techniques utilized and the color codes in the detailed botanical description accurately describe the new *Helleborus*.

DETAILED BOTANICAL DESCRIPTION OF THE PLANT

The following is a detailed description of two year-old plants of 'Amor' as field grown outdoors in Reeuwijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Approximately 8 weeks beginning in late fall to early winter in Reeuwijk, The Netherlands.

*Plant type.*—Herbaceous perennial.

*Plant habit.*—Upright and outward, acaulescent (stemless) with flowering stems (peduncles) emerging from rootstock.

*Height and spread.*—An average of 35 cm in height and 80 m in width.

*Cold hardiness.*—At least in U.S.D.A. Zone 5.

*Diseases and pests.*—No unique resistance or susceptibility to diseases or pests has been observed.

*Root description.*—Fleshy, fibrous, and fine.

*Growth rate.*—Moderate, an average of 7 cm in spring.

*Root development*—A rooted plantlet produced by tissue culture will fully develop in an 11-cm container in about 6 months.

*Propagation.*—Tissue culture (preferred) and division.

Foliage description:

*Leaf shape.*—Leaf; palmate, orbicular in outline, leaflet; obovate and 2- to 3-cleft.

*Leaf division.*—Compound.

*Leaf arrangement*—Emerge from basal rosettes.

*Leaf quantity.*—An average of 6 leaves per rosette and 5 leaflets per leaf.

*Leaf size.*—Leaf; an average of 20.8 cm in length and width, leaflet; an average of 14.2 cm in length and 6.3 cm in width.

*Leaf base.*—Leaf; hastate, leaflet; narrowly cuneate.

*Leaf and leaflet apex.*—Acute.

*Leaf and leaflet margins.*—Serrate.

*Leaf venation.*—Pinnate, with secondary veins reticulate, color; 144B and N144A and lower surface 144C.

*Leaf surface.*—Upper and lower surfaces; glabrous and very slightly shiny.

*Leaf color.*—Young upper surface; 137B, young lower surface; 147B, mature upper surface; N137B to N137C, mature lower surface; a blend of 144B and N144A.

*Leaf fragrance.*—None.

*Petioles.*—Up to 26.8 cm in length and 6 mm in width, 144A in color, glabrous surface.

Flower description:

*Inflorescence type.*—Compound panicle of single rotate flowers.

*Inflorescence size.*—An average of 23.4 cm in height and 11.1 cm in width.

*Lastingness of flower.*—An average of 10 days, sepals persistent, other parts self-cleaning.

*Flower fragrance.*—None.

*Flower number.*—An average of 6 per flowering stem.

*Flower aspect.*—Nodding to slightly outward.

*Flower bud.*—An average of 2.4 cm in length and 1.5 cm in width, flattened ovate in shape, color; N77B with veins N77A tinged with 146B at the base.

*Flower form.*—Single, rotate with a small inner ring of petals and showy sepals, pistils, and stamens.

*Flower size.*—An average of 2.6 cm in height and 5.4 cm in diameter.

*Sepals.*—5, showy, orbicular in shape, rotate arrangement, held horizontally when fully open, overlapping, about 3.1 cm in length and width, apex rounded, base broadly cuneate, entire margins, upper and lower surfaces is dull and smooth, color; immature upper surface N77B with base 145A to 145B, immature lower surface N77B with veins N77A and base tinged 146B, mature upper surface a blend between 70B and N77B with base 145B, mature lower surface N77B to N77A with veins N77A and base tinged 146B.

*Petals.*—About 14, transformed into nectaries, rotate arrangement, flattened triangular tube shape, form a single slightly overlapping, upright ring around at base of stamens held horizontally when fully open, about 8 mm in length and 5 mm in width, circular truncate apex (top of tube) curved inward, base broadly attenuate, inner and outer surfaces smooth and slightly glossy, color; inner and outer surface; 144C with base N144C, color not fading.

*Peduncles (flowering stems).*—Rounded in shape, moderately strong, an average of 15.5 cm in length and 5 mm in width, held at an average angle of 80° to upright, color; 144C heavily marbled with 187A to 187B, peduncle leaves; present at terminus and branch points of peduncle, pedate in shape, about 3 cm in width and 2 cm in length, 3 to 5 leaflets; oblanceolate in shape, acute apex, truncate base, finely serrate margins, upper surface and lower surface glabrous, color upper and lower surface; 144A to 144B and tinged with 187B on lower surface.

*Pedicels.*—Rounded in shape, moderately strong, curved outward at about a 30° angle, an average of 2.2 cm in length and 2 mm in width, color 144C heavily marbled with 187A.

Reproductive organs:

*Gynoecium.*—5 pistils, an average of 1.5 cm in length, stigma is club-shaped and 157A in color, style is about 1.4 cm in length and 183C in color, ovary is 150C in color.

*Androcoecium.*—About 70 stamens, anthers are basifixed and double-kidney shaped, 4 mm in length and 155A in color, filaments are 1.7 mm in length and 157D in color, pollen is moderate to abundant in quantity and 155A in color.

*Fruit/seeds.*—None detected to date.

It is claimed:

1. A new and distinct cultivar of *Helleborus* plant named 'Amor' as herein illustrated and described.

* * * * *